US005778893A

United States Patent [19]
Potter

[11] Patent Number: 5,778,893
[45] Date of Patent: Jul. 14, 1998

[54] METHOD OF DIAGNOSING AND MONITORING A TREATMENT FOR ALZHEIMER'S DISEASE

[75] Inventor: Huntington Potter, Boston, Mass.

[73] Assignee: President and Fellows of Harvard College, Cambridge, Mass.

[21] Appl. No.: 446,529

[22] Filed: May 19, 1995

Related U.S. Application Data

[63] Continuation-in-part of Ser. No. 409,103, Mar. 24, 1995, Pat. No. 5,535,760, which is a continuation of Ser. No. 109,746, Aug. 20, 1993, abandoned, which is a continuation-in-part of Ser. No. 678,683, Apr. 1, 1991, Pat. No. 5,297,562.

[51] Int. Cl.$^6$ ................................................ A61B 19/00
[52] U.S. Cl. ................................................ 128/898
[58] Field of Search ................................ 128/897–898; 424/9

[56] References Cited

U.S. PATENT DOCUMENTS

| | | | |
|---|---|---|---|
| 5,297,562 | 3/1994 | Potter | 128/898 |
| 5,535,760 | 7/1996 | Potter | 128/898 |

OTHER PUBLICATIONS

Potter, H., "Review and Hypothesis: Alzheimer Disease and Down Syndrome–Chromosome 21 Nondisjunction may Underlie Both Disorders," *Am. J. Hum. Genet.*, 48:1192–1200 (1991).

Inzelberg, R., et al., "Effects of Atropine on Learning and Memory Functions in Dementia," *Clinical Neuropharmacology*, 13(3):241–247 (1990).

Schweber, M.S., "Alzheimer's Disease and Down Syndrome," *Progress in Clinical and Biol. Research*, 317:247–267 (Alan R. Liss, Inc., 1989).

Lichter, P., et al., "Rapid Detection of Human Chromosome 21 Aberrations by in situ Hybridization," *Proc. Natl. Acad. Sci. USA*, 85:9664–9668 (1988).

Talamo, B.R., et al., "Pathological Changes in Olfactory Neurons in Patients with Alzheimer's Disease," *Nature*, 337:736–739 (1989).

Schweber, M., "A Possible Unitary Genetic Hypothesis for Alzheimer's Disease and Down Syndrome," *Anals of NY Acad. Sciences*, 450:223–238 (1985).

Madan, K., et al., "Premature Centromere Division (PCD): A Dominantly Inherited Cytogenetic Anomaly," *Hum. Genet.*, 77:193–196 (1987).

Jabs, E.W., et al., "Centromere Separation and Aneuploidy in Human Mitotic Mutants: Roberts Syndrome," *Mechanisms of Chrom. Dist. and Aneuploidy*, 111–118 (Alan R. Liss, Inc., 1989).

Uchida, I.A., et al., "Chromosome Aberrations Induced in vitryo by Low Doses of Radiation: Nondisjunction in Lymphocytes of Young Adults," *Am. J. Hum. Genet.*, 27:419–429 (1975).

Romke, C., et al., "Roberts Syndrome and SC Phocomelia. A Single Genetic Entity," *Clinical Genetics*, 31:170–177 (1987).

Moorhead, P.S., and Heyman, A., "Chromosome Studies of Patients with Alzheimer Disease," *Amer. J. Of Med. Genet.*, 14–545–556, (1983).

Evans, D.A., et al., "Prevalence of Alzheimer's Disease in a Community Population of Older Persons," *JAMA*, 262(18): 2551–2556 (1989).

Jarvik, L.F., et al., "Chromosomes and Mental Status," *Arch. Gen. Psychiatry*, 30:186–190 (1974).

Matsuyama, S.S., and Jarvik, L.F., "Hypothesis: Microtubules, a Key to Alzheimer Disease," *Proc. Natl. Acad. Sci. USA*, 86:8152–8156 (1989). Nordenson, I., et al., "Chromosomal Abnormality in Dementia of Alzheimer Type," *The Lancet*, 481–482 (Mar. 1, 1989).

Buckton, K.E., et al., "Chromosome Changes in Alzheimer's Presenile Dementia," *J. of Med. Genet.*, 20:46–51 (1983).

Ward, B.E., et al., "Increased Aneuploidy in Alzheimer Disease," *Amer. J. Of Med. Genet.*, 3:137–144 (1979).

White, B.J., et al., "Cytogenetic Studies of Familial and Sporadic Alzheimer Disease," *Amer. J. of Med. Genet.*, 10:77–89 (1981).

Heston, L.L., and Mastri, A.R., "The Genetics of Alzheimer's Disease," *Arch. Gen. Psychiatry*, 34:976–981 (1977). Heston, L.L., et al., "Dementia of the Alzheimer Type," *Arch. Gen. Psychiatry*, 38:1085–1090 (1981).

Lai, F., and Williams, R.S., "A Prospective Study of Alzheimer Disease in Down Syndrome," *Arch. Neurol.*, 46:849–853 (1989).

Pagon, R.A., et al., "Abnormal Skin Fibroblast Cytogenetics in Four Dysmorphic Patients with Normal Lymphocyte Chromosomes," *Am. J. Hum. Genet.*, 31:54–61 (1979).

Goate, A.M., et al., "Predisposing Locus for Alzheimer's Disease on Chromosome 21," *The Lancet*, 352–355 (Feb. 18, 1989).

Peters, G.B., et al., "Trisomy 21 Mosaicism and Maternal Age Effect," *The Lancet*, 1202–1203 (May 23, 1987).

Robison, S.H., et al., "Alzheimer's Disease Cells Exhibit Defective Repair of Alkylating Agent–Induced DNA Damage," *Anals of Neurology*, 21(3):250–258 (1987).

Hardy, J., et al., "Presenile Dementia Associated with Mosaic Trisomy 21 in a Patient with a Down Syndrome Child," *The Lancet*, 743 (Sep. 23, 1989).

(List continued on next page.)

*Primary Examiner*—John P. Lacyk
*Attorney, Agent, or Firm*—Hamilton, Brook, Smith & Reynolds, P.C.

[57] ABSTRACT

The present invention is a method of diagnosing Alzheimer's Disease in an individual. The method comprises administering an agent which alters neuromuscular signalling to an individual being tested for Alzheimer's Disease. The administration of the agent causes a physiological response in individuals with Alzheimer's Disease which differs in degree or magnitude from normal individuals. Because the extent of the difference is indicative of the severity of the disease, the invention can also be used to monitor the response of an individual with Alzheimer's Disease to treatment and also to identify new treatments.

24 Claims, 6 Drawing Sheets

OTHER PUBLICATIONS

Rowe, I.F., et al., "Presenile Dementia Associated with Mosaic Trisomy 21 in a Patient with a Down Syndrome Child," *The Lancet*, 229 (Jul. 22, 1989).

Harris, W.S. and Goodman, R.M., "Hyper-Reactivity to Atropine in Down's Syndrome," *N.E. J. of Med.*, 279(8) : 407–410 (1968).

Fitzgerald, P.H., et al., "Evidence for the Repeated Primay Non–Disjunction of Chromosome 21 as a Result of Premature Centromere Division (PCD)," *Hum. Genet.*, 72:58–62 (1986).

Sacks, B. and Smith S., "People with Down's Syndrome can be Distinguished on the Basis of Cholinergic Dysfunction," *J. of Neurology, Neurosurgery, and Psych.*, 52:1294–1295 (1989).

Berg, J.W., et al., "Atropine in Mogolism," *Lancet*, 2:441–442 (1959).

Geller, L.N., et al., "Genetic and Clinical Links between Trisomy 21, Down Syndrome and Alzheimer's Disease," *Society for Neuroscience Abstracts*, Abstract #515.8, p. 1255 (1993).

Geller, L.N., et al., "Genetic and Clinical Links Between Trisomy 21, Down Syndrome, and Alzheimer's Disease," *The American Society for Cell Biology*, 4:246A Abstract #1426 (Dec. 1993).

Geller, L.N., et al., "Genetic and Clinical Links between Trisomy 21, Down Syndrome and Alzheimer's Disease," *Amer. J. of Human Genet.*, 53, Sep. 1993 (Supplement), Abstract #548.

Rapley, et al., *Lancet*:1202: (May 23, 1987).

Katz, B., et al., "Cholineric Supersensitivity of the Iris Sphincter in alzheimer's Disease," *Ophthal.*, 95:134 (Sep. 1988 Supp).

Sitaram, N. and Pomara, N., "Increased Pupillary Miotic Response to Pilocarpine in cognitively Impaired Elderly Subjects," *ICRS Medical Science*, 9:409–410 (1981).

● Patients with Probable Alzheimer's Disease
○ Normal Elderly Controls

METHOD OF DIAGNOSING AND MONITORING A TREATMENT FOR ALZHEIMER'S DISEASE

RELATED APPLICATION

This application is a Continuation-In-Part of U.S. Ser. No. 08/409,103, filed Mar. 24, 1995, now U.S. Pat. No. 5,535,760 which is a File Wrapper Continuing Application of U.S. Ser. No. 08/109,746, filed Aug. 20, 1993, now abn, which is a Continuation-In-Part of U.S. Ser. No. 07/678,683, filed on Apr. 1, 1991, now U.S. Pat. No. 5,297,562. The teachings of these previously filed applications are incorporated herein by reference.

FUNDING

Work described herein was supported in part by National Institutes of Health Grant #AG09665 and #AG08084. The U.S. Government has certain rights in the invention.

BACKGROUND OF THE INVENTION

It has been appreciated for some time that Alzheimer's Disease has a complex etiology. At least 15 percent of the cases appear to be due to the inheritance of an autosomal-dominant mutation, but the majority are "sporadic", showing no clear association with any identifiable genetic or environmental factor. Feldman, R. G., et al., *Neurology*, 13:811–824 1963; Heston, L. L., et al., *Arch Gen. Psychiat.*, 38:1084–1090 (1981); Terry, R. D., *Aging*, 7:11–14 (1978); Jarvik, L. F. and Matsuyama, S. S., "The Biological Substrates of Alzheimer's Disease", Academic Press, pp. 17–20 (1986). Even identical twins can show a large discordance in the age of onset of the disease. Nee, L. E., et al., *Neurology*, 37:359–363 (1987). Yet despite this variation, Alzheimer's Disease shows a uniform set of clinical and pathological features progressive loss of memory and other intellectual functions beginning in middle to late life, coupled with neuronal cell loss in the higher centers of the brain. Price, D. L., *Ann. Rev. Neurosci.*, 9:489–512 (1986).

Although the loss of memory and other intellectual functions associated with Alzheimer's Disease are well documented, methods of diagnosing the disease have serious shortcomings. This is due to the laborious and time consuming cognitive tests that are required. Furthermore, methods of diagnosing the disease can be inaccurate because other ailments commonly associated with later life can also cause loss of cognitive functions. Consequently, there is a need for more efficient and accurate methods of diagnosing Alzheimer's Disease.

Measuring the response of an individual to a treatment and identifying new treatments requires an ability to monitor the progression of the disease. However, the same cognitive tests required to diagnose Alzheimer's Disease are used to measure the severity of the disease in an individual. Therefore, there also exists a need for more accurate and efficient methods of measuring the severity of Alzheimer's Disease.

SUMMARY OF THE INVENTION

One embodiment of the present invention is a method of assessing Alzheimer's Disease in an individual, including aiding in the diagnosis of Alzheimer's Disease in an individual and aiding in determining the prognosis of the individual. The method comprises administering to a test individual (i.e., an individual being tested for Alzheimer's Disease) an agent which alters neuromuscular signalling to a different extent (e.g. greater or lesser) in an individual with Alzheimer's Disease than in an individual without Alzheimer's Disease. As a result, a physiological response is induced in the test individual that is quantitatively different (e.g. greater or lesser) in the test individual from the physiological response in an individual without Alzheimer's Disease to whom the agent has been administered under the same conditions (e.g., in the same amount). A sufficient amount of the agent is an amount which causes a physiological response caused by the same amount of agent in an individual, either a person with Alzheimer's Disease, a person without Alzheimer's Disease, or both. The extent (or degree) of the physiological response is assessed after a period of time which is sufficient to allow the agent to cause the physiological response. The extent or degree of the physiological response in the test individual is compared with an appropriate control (i.e., an individual or population of individuals who do not have Alzheimer's Disease to whom the same agent has been administered in the same amount and whose physiological response thereto has been assessed after the same time period). A greater or lesser physiological response in the test individual compared with the reference is indicative of Alzheimer's Disease in the test individual. Alternatively, the rate of the physiological response is determined in the test individual and compared with the rate of the same response in an appropriate control. A rate of response which differs (e.g. is more rapid or slower) in the test individual compared with the control is indicative of Alzheimer's Disease in the test individual. Such agents as cholinergic antagonists, adrenergic agonists and adrenergic antagonists can be used and are preferably administered to the eyes in order to cause a change in pupil diameter.

The extent or rate of physiological response of the test individual can also be compared to the extent or rate of the response in an appropriate group of individuals with Alzheimer's Disease having similar attributes (e.g., age, sex, ethnicity) to the test individual. This group is referred to as a reference group. A similar extent or rate of physiological response in the test individual compared with the reference is indicative of Alzheimer's Disease in the test individual. The physiological responses and attributes of the test individual and reference can be stored in a database. Optionally, the database can be searched by computer means. One implementation of this embodiment is also disclosed.

Another embodiment of the present invention is a method of monitoring the response of an individual to a treatment for Alzheimer's Disease. A third embodiment is a method of identifying an agent effective for treatment of Alzheimer's Disease. In both of these methods, the difference between the extent or rate of a physiological response of a test individual prior to treatment and of an appropriate control to an agent which alters neuromuscular signalling is determined. The difference between the rate or extent of the same physiological response of the test individual after treatment and the response of the appropriate control to the same agent, referred to as a second difference, is determined. The two differences are then compared. If the second difference compared with the first difference decreases, remains the same, or increases at a rate less than is typically observed for untreated individuals with Alzheimer's Disease, the treatment is one which reverses, arrests, or slows the progression, respectively, of the disease in the test individual.

Another embodiment of the present invention is a method of identifying more sensitive agents for the diagnosis of Alzheimer's Disease. The method comprises determining the difference (i.e., the first difference) between the extent of a physiological response in an individual with Alzheimer's Disease and a control individual to an agent (i.e., the diagnostic agent) which alters neuromuscular signalling. The difference (i.e., the second difference) between the rate or extent of the physiological response in the individual with Alzheimer's Disease and the control individual to the agent being tested for its ability to diagnosis Alzheimer's Disease is determined. The test agent is more sensitive than the diagnostic agent for diagnosing Alzheimer's Disease when the second difference is greater than the first difference.

A further subject of the present invention is a kit comprising an agent which causes a greater or lesser physiological response in an individual with Alzheimer's Disease than in a person without Alzheimer's Disease and an apparatus for administering the agent to an individual.

The present invention has many advantages. The method enables the diagnosis of Alzheimer's Disease before the onset of symptoms associated with the disease. It also makes it possible to determine the severity of the disease in an individual. Because the method can be performed in a short period of time and does not require extensive cognitive tests presently used to determine the severity of the disease, the method can be used more easily to monitor the response of an individual to treatment and identify new treatments.

BRIEF DESCRIPTION OF THE DRAWING

FIG. 1 shows in graphical form the percent change in pupil diameter of the treated eye versus the untreated eye at eight different sampling intervals occurring at 0, 2.5, 8, 15, 22, 29 41 and 53 minutes. FIG. 1 also compares the change in pupil diameter of patient's diagnosed as probable Alzheimer's patients (-♦- AD) and patients without the symptoms characteristic of Alzheimer's Disease (-■- CN) - - -.

DETAILED DESCRIPTION OF THE INVENTION

Figure 1:
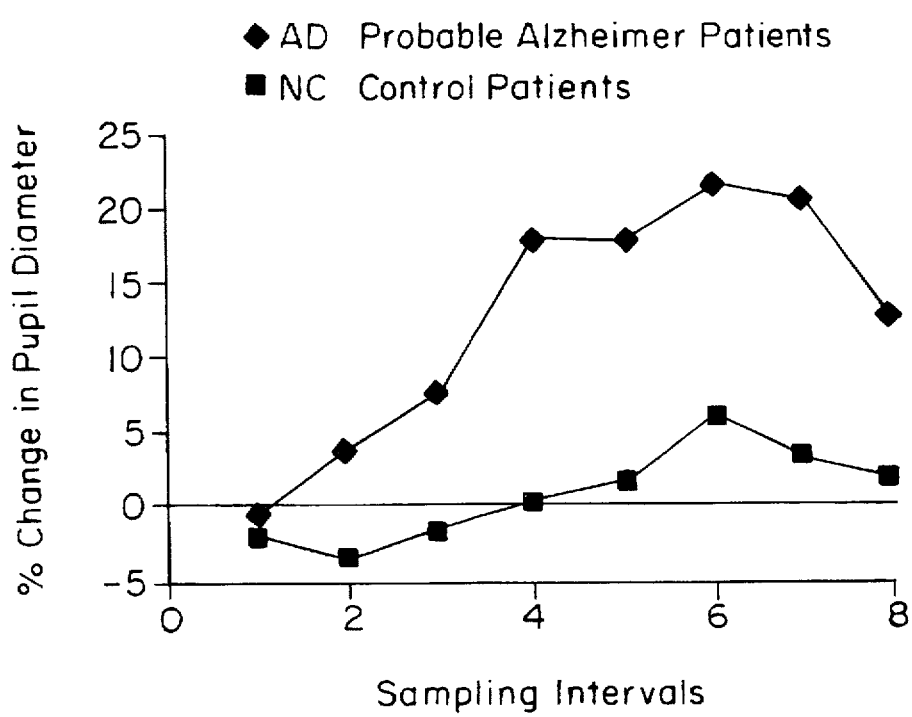
FIG. 1 is a graph representing results obtained in studies of mydriasis following tropicamide administration to one eye in each of five patients diagnosed as probable Alzheimer's patients and 13 negative control patients who did not exhibit symptoms characteristic of Alzheimer's Disease.

Applicant has shown that agents which alter neuromuscular signalling in individuals cause alterations which are different (e.g., greater or lesser) in individuals with Alzheimer's Disease than in individuals without Alzheimer's Disease. Such an agent induces a physiological response in an individual with Alzheimer's Disease that is quantitatively different (greater or lesser) from the response to the same agent in an individual without Alzheimer's Disease. This difference can be identified and measured and serves as the basis for a method of diagnosing Alzheimer's Disease in an individual. The magnitude or extent of the difference is a measure of the severity of Alzheimer's Disease in the individual and can be used in a method of monitoring the response of an individual to a treatment for Alzheimer's Disease and in a method of identifying new treatments for Alzheimer's Disease.

As described in prior applications, Ser. Nos. 08/109,746 and 07/678,683, now U.S. Pat. No. 5,297,562, pupil dilation is different in response to the administration of cholinergic antagonists, particularly tropicamide, in individuals with Alzheimer's Disease compared with individuals without Alzheimer's Disease. Specifically, pupil dilation is greater in individuals with Alzheimer's Disease than in individuals without Alzheimer's Disease. In fact, a difference in pupil dilation in response to tropicamide was observed between control individuals and an individual who appeared not to have Alzheimer's Disease, but later developed symptoms characteristic of Alzheimer's Disease. Thus, a cholinergic antagonist can be administered to the eyes to diagnose Alzheimer's Disease before the onset of symptoms now used to diagnose the disease. More generally, this result shows that changes in intercellular communication or signalling occur that can be detected in the peripheral areas of the body in individuals with Alzheimer's Disease in addition to the brain and that the presence of such changes in the periphery is indicative of the effects of the Alzheimer's Disease in the brain. "Peripheral areas of the body" refers to areas of the body other than the brain.

Cholinergic antagonists alter neuromuscular signalling in the eyes of an individual. Neuromuscular signalling in the eye is affected differently in those with Alzheimer's Disease than in those without. The effect of the alteration is greater in individuals with Alzheimer's Disease than in normal individuals, that is, the extent to which neuromuscular signalling in the eyes is affected is greater in an individual with Alzheimer's Disease than in an individual without the condition. This result is consistent with the statement in the earlier filed applications that other physiological responses under the neuromuscular control of a cholinergic neurotransmitter will be differentially affected by cholinergic antagonists. In addition, the rate at which the physiological response is affected differs in individuals with Alzheimer's Disease compared with disease free individuals.

"Neuromuscular signalling" refers to neurotransmission signalling and neuromuscular control. "Neurotransmission signalling" is neurochemical communication from neuron to neuron. Examples of neurotransmission signalling include the release of neurotransmitters, such as dopamine, acetyl choline and serotonin from the nerve terminus into the synapse and the diffusion of the neurotransmitters across to the synapse to the post synaptic receptor of the adjoining neuron. "Neuromuscular control" refers to systems involved in neurochemical communication between neurons and muscles. Examples of neuromuscular control include acetyl choline, epinephrine, adrenalin, serotonin and nitric oxide.

As used herein, "physiological response" refers to the activity or inhibition of previous activity of an organism or any of its parts resulting from stimulation. In the present invention, stimulation is typically caused by administering an agent which alters neuromuscular signalling. Examples of physiological responses include heart rate, sweat production, pupil dilation and saliva production. "Assessing" a physiological response refers to making a measure of the extent (or degree) or rate of the physiological response. Measuring the extent or rate of the physiological response can be done quantitatively or estimated, for example by observation. In the case of pupil dilation, for example, the physiological response can be assessed by measuring the pupil diameter. In the case of heart rate, the physiological response can be assessed, for example, by determining the number of heart beats per period of time.

As used herein, "differentially affecting a physiological response" refers to causing, for example by administration of an agent, a physiological response which is quantitatively different (greater or lesser) in an individual with Alzheimer's Disease than in an individual without Alzheimer's Disease in response to the agent. A physiological response that is differentially affected is also referred to as a "differential physiological response." Assessing whether an individual has a differential response following the administration of one of these agents compared with individuals without Alzheimer's Disease can, therefore, also serve as a method of diagnosing Alzheimer's Disease. "Altering neuromuscular signalling" means that neuromuscular signalling is stimulated, enhanced, suppressed, inhibited or modulated. Agents which alter neuromuscular signalling are, for example, agonists, antagonists or inhibitors of systems involved in neuromuscular signalling.

As used herein, the "rate at which a physiological response is affected" is how quickly (or slowly) the physiological response changes following the administration of an agent which alters neuromuscular signalling. Alternatively, the "rate at which a physiologically response is affected" is how quickly (or slowly) a response returns to its "normal" or pre-altered state after having been changed by the administration of an agent which alters neuromuscular signalling.

Adrenergic receptors often balance the effects of cholinergic receptors, in particular muscarinic receptors, in the autonomic nervous system. One example of the balancing of effects is evident in control of pupil diameter in the eye, where antagonists of muscarinic receptors cause pupil dilation while antagonists of adrenergic receptors cause constriction of the pupil. Because abnormal control of neuromuscular signalling is evident in an eye of an individual with Alzheimer's Disease upon application of a muscarinic receptor antagonist, abnormal control of neuromuscular signalling will also be evident in response to the application of an adrenergic receptor agonist or antagonist, which, as discussed above, are known to balance the function of the muscarinic receptors in the eye. Other physiological responses under the control of the autonomic nervous system in which muscarinic and adrenergic receptors balance the functions of the other will also show differential responses in individuals with Alzheimer's Disease after the administration of adrenergic agonists or antagonists. Examples of such physiological responses include rate of heart beat, blood vessel dilation and relaxation, blood pressure and saliva production.

Apparently, changes occur in neuromuscular signalling in individuals with Alzheimer's Disease. As a result, differential physiological responses occur in the peripheral areas of the body in individuals with Alzheimer's Disease that reflect the changes in the brain. Denervation supersensitivity due to a lack of neurons and/or axons may also be responsible for these differential responses. Applicant has shown that the changes that occur in neuromuscular signalling are detectable before the cognitive degeneration resulting from changes in the brain becomes evident. Consequently, detecting and, optionally, quantitating differential physiological responses resulting from Alzheimer's Disease induced changes in neuromuscular signalling has many uses, including early detection of the disease, monitoring treatment and identifying new and improved treatments. Additionally, detecting and/or quantitating differential physiological responses after the cognitive degeneration resulting from Alzheimer's Disease becomes evident can supplement or supplant conventional methods of diagnosing Alzheimer's Disease such as the NINCDS-ADRDA diagnostic criteria for Alzheimer's Disease.

Abnormalities in other peripheral areas of the body will occur in individuals with Alzheimer's Disease and that these abnormalities are associated with defects in systems involved in neuromuscular signalling other than cholinergic- and adrenergic-mediated systems. Such systems include intracellular signalling systems, neuromodulatory systems, acetylcholine esterase, calcium metabolism, calcium transport and sodium and potassium transport involved in nerve and muscle function. Administering an agonist, antagonist or inhibitor (in the case of an enzyme such as acetyl cholinesterase) of these other systems to an individual with Alzheimer's Disease will cause physiological responses which are quantitatively different from those in individuals without Alzheimer's Disease. Quantitating these physiological responses makes it possible to identify individuals with Alzheimer's Disease.

One embodiment of the present invention is a method of testing for Alzheimer's Disease in an individual. The method can also aid in the diagnosis of Alzheimer's Disease in an individual and aid in determining the prognosis of an individual with Alzheimer's Disease. An agent or drug which alters neuromuscular signalling in an individual is administered to an individual being tested for Alzheimer's Disease. The individual being tested for Alzheimer's Disease is referred to as the "test individual". In one embodiment, the agent or drug is administered in an amount sufficient to cause a physiological response in an individual, either a person with Alzheimer's Disease, a person without Alzheimer's Disease or both. After a period of time which is sufficient to allow the physiological response to occur, the degree, extent or rate of the physiological response is assessed or measured. As used herein, "period of time" can be one specific time interval at which the physiological response is assessed or a time course over which the physiological response is assessed at more than one interval. Thus, the measurement can be a single point measurement or a series of measurements. The extent or rate of the physiological response is compared to the rate or extent of response in an appropriate control. A greater or lesser response in the test individual compared with the control is indicative of Alzheimer's Disease in the test individual.

In certain instances physiological responses may occur after administration of an agent which alters neuromuscular signalling in individuals with Alzheimer's Disease that do not occur in normal individuals. In other instances it may be possible to adjust the amount of the agent being administered so that a physiological response occurs in an individual with Alzheimer's Disease but not in a normal individual. In such cases, the presence of a physiological response in a test individual but not in a control individual is indicative of Alzheimer's Disease in the test individual.

The method of the present invention of testing for Alzheimer's Disease in an individual can be used in conjunction with other tests presently employed for diagnosing the disease and determining the prognosis of an individual with the disease, e.g. the NINCDS-ADRDA diagnostic criteria. Consequently, the method can be one of a number of tests used, i.e. it can be used as an aid, to determine whether an individual has Alzheimer's Disease and the individual's prognosis.

Assessment of the effects of an agent on individuals without Alzheimer's Disease can be carried out before, after or simultaneously with the assessment of its effects on the test individual. The assessment of the individual without Alzheimer's Disease is carried out under the same conditions (e.g., same dose of the agent which alters neuromuscular signalling and assessment of the same physiological response after the same period of time after administration of the agent), as the assessment of the test individual. The "appropriate control" can also be a standard which has been established based on the assessment of the physiological response of an appropriate population of individuals without Alzheimer's Disease to the agent which alters neuromuscular signalling. The assessment of the population is carried out under the same conditions as the assessment of the test individual, as described above.

An "appropriate reference" group is a subset of individuals with Alzheimer's Disease having attributes similar to those of the test individual. As used herein, "attributes" refer to characteristics of an individual which have been shown to correlate with an increased or decreased likelihood of an individual developing Alzheimer's Disease. Age is an example of an attribute. For example, individuals over 70 years of age are about ten times more likely to have Alzheimer's Disease in some form than those aged between 30–59. Other attributes include sex and ethnicity. It is to be understood that as research progresses, other attributes will be identified. These are encompassed within the present invention.

The subset can also include individuals with predementia Alzheimer's Disease who have attributes similar to those of the test individual. An individual with "predementia Alzheimer's Disease" does not have the dementia associated with Alzheimer's Disease, has a differential response following the administration of an agent which alters neuromuscular signalling, as described herein, and later develops the dementia associated with Alzheimer's Disease.

The extent or degree of the physiological response of the test individual following the administration of the agent which alters neuromuscular signalling is compared with the rate or extent of the physiological responses of the reference. A degree or extent of the physiological response in the test individual that is similar to the degree or extent of the physiological response of the appropriate reference is indicative of Alzheimer's Disease in the test individual. In the case where the test individual is otherwise asymptomatic of Alzheimer's Disease, a rate or extent of physiological response that is similar to a reference group of predementia Alzheimer's Disease individual's is indicative that the test individual has predementia Alzheimer's Disease.

In one aspect of the present invention, the extent or rate of physiological responses of individuals and their attributes are stored in a database. The database is searched to identify an appropriate reference for the test individual being assessed. In a preferred embodiment, the database is stored in a computer. The database is searched by a computer means for a subset of individuals (i.e., appropriate reference) having attributes similar to the test individual. The physiological responses for the subset and test individual are compared by computer means to determine whether the test individual has Alzheimer's Disease.

An agent which alters neuromuscular signalling in an individual with Alzheimer's Disease can be tested for its suitability for use in diagnosing Alzheimer's Disease by identifying a physiological response which this agent modulates or affects. The agent is then administered to an individual with Alzheimer's Disease and to a control individual (i.e., an individual without Alzheimer's Disease) in an amount suitable to alter the physiological response in the control individual. The physiological response is then assessed in the control individual and in the individual with Alzheimer's Disease. When the degree or extent of the physiological response in the individual with Alzheimer's Disease is found to differ (i.e. is greater or lesser than the response in the control individual), the agent is suitable for use in diagnosing Alzheimer's Disease. It is to be understood that it is not always possible to predict whether the physiological response will be greater in the individual with Alzheimer's Disease than in the control individual or lesser. It is even possible that certain physiological responses observed in individuals with Alzheimer's Disease will not be evident in control individuals. Whether the physiological response is greater or lesser is unimportant. What is significant is the fact that Alzheimer's Disease also causes changes in areas of the body besides the brain. These changes are manifested by physiological responses that differ in magnitude from those which occur in normal individuals following the administration of agents which alter the neuromuscular signalling that controls the responses. The important factor for the methods of the present invention is that these differential physiological responses can be identified, detected and, optionally, quantitated.

There are many physiological responses on which the diagnostic test for Alzheimer's Disease of the present embodiment can be based. Suitable physiological responses include those under the neuromuscular control of cholinergic antagonists, adrenergic agonists or adrenergic antagonists. One suitable physiological response is a change in pupil diameter. Other suitable physiological responses include sweat production, saliva production, heart rate and blood pressure. Physiological responses are generally chosen to maximize the ease of assessing the degree of the response. Physiological responses under the control of other agents include nociception (pain), touch, cardiac function, neuromuscular tone and neuroendocrine control.

Agents suitable for use in the method of the present embodiment for diagnosing an individual with Alzheimer's Disease include cholinergic antagonists, adrenergic agonists or antagonists, acetylcholinesterase inhibitors, agonists and antagonists of intracellular signalling systems, agonists and antagonists of neuromodulatory systems, agonists and antagonists of calcium metabolism and calcium channels, agonist and antagonists of sodium and potassium channels involved in nerve and muscle function and light.

Suitable cholinergic antagonists which can be tested for use as a diagnostic for Alzheimer's Disease include pirenzepine, scopolamine, quinuclidinyl benzilate, bungarotoxin, cobratoxin, pancuronium, curare and the like. Suitable adrenergic agonists which can be tested for use as a diagnostic for Alzheimer's Disease include epinephrine, clonidine and the like. Suitable adrenergic antagonists which can be tested for use as a diagnostic for Alzheimer's Disease include propranolol, phentolamine and the like.

Suitable acetylcholinesterase inhibitors include tacrine, physostigmine, DFP (diisofluorophosphate), and related compounds.

Suitable agonists of intramolecular signalling systems include forskolin. Suitable antagonists of intramolecular signalling systems include lithium and pertussis toxin. Also included in intramolecular signalling systems are agonists and antagonist of kinases and phosphatases, okadaic acid, phorbol esters and the like.

Suitable agonists and antagonists of neuromodulatory systems include those agonists and antagonists which modulate systems involving amines (such as serotonin and dopamine), peptide hormones, adenosine, γ-amino butyric acid (GABA), glutamate, nitric oxide, carbon monoxide and the like. Agents which act as agonists for the receptors of these systems include N-methyl d-aspartate (NMDA), kainate, benzodiazepines, barbiturates, thioxanthene and the like. Agents which act as antagonists for the receptors of these systems include clozapine, phenothiazine reserpine, and the like. Also included are antagonists and agonists which modulate the uptake and processing of neurotransmitters. Examples of such antagonists include cocaine, Prozac, imipramine, fluoxetine, clorgyline, reserpine, amphetamine, pargyline, Rolpram, and the like.

Calcium metabolism and calcium channels, as used herein, refers to voltage-sensitive calcium channels, the N-methyl d-aspartate receptor and inositol triphosphate dependent release of calcium from intracellular stores. Suitable agonists include N-methyl d-aspartate, glutamate and lithium. Suitable antagonists include APV (2-amino-5-phosphonovalerate), conotoxin, various spider toxins, nitrendopine, dihydropyridine, digitalis, and the like.

The terms sodium channels and potassium channels, as used herein, refer to those channels involved in nerve and muscle function. Suitable antagonists include tetrodotoxin and tetraethyl-ammonium ions.

In one embodiment of the present invention, the agent is a cholinergic antagonist, an adrenergic agonist or an adrenergic antagonist. It has been shown previously by Applicant that cholinergic antagonists cause pupil dilation in the eyes of individuals with Alzheimer's Disease that is greater than in normal individuals. Physiological responses other than pupillary response under the control of cholinergic antagonists will also be differentially affected. Further, because adrenergic receptors often balance the effects of cholinergic receptors, physiological responses other than pupil diameter will be differentially affected by adrenergic agonists and antagonists. Physiological responses caused by light, for example pupil constriction, will show also similar differential affects.

In another embodiment of the present invention the agent used is one which alters neuromuscular signalling in the eyes of an individual. The agent is administered to a test individual in an amount suitable to cause a change in pupil diameter in an individual, either a person with Alzheimer's Disease, a person without Alzheimer's Disease or both. The pupil diameter of one or both eyes of the test individual is measured after a period of time sufficient to allow the agent to alter neuromuscular signalling. The pupil diameter for the test individual is compared with that of an appropriate reference. A change in the pupil diameter in the eye(s) of the test individual that differs from the change observed in the reference is indicative of Alzheimer's Disease in the test individual. Some agents may cause changes in pupil diameter in an eye of an individual with Alzheimer's Disease but have no effect on the pupil diameter in control individuals (i.e., individuals without Alzheimer's Disease). Alternatively, it may be possible to administer an amount of the agent which causes no change or a minimal but detectable change in pupil diameter in a control individual, but which causes a change in an individual with Alzheimer's Disease. In these cases, a change in pupil diameter in a test individual but not in a control individual is indicative of Alzheimer's Disease in the test individual.

Preferably, the agent is administered to an eye of the control individual(s) and to an eye of the test individual. In one aspect, the agent is a cholinergic antagonist, such as tropicamide. Solutions containing from about 0.002% to about 0.07% tropicamide are suitable, with concentrations of about 0.009% to about 0.011% being preferred. When a solution of 0.01% tropicamide is used, the pupil diameter of the eye can be determined about 15–45 minutes after administration, preferably at about 30 minutes. Alternatively, both eyes of the control individual(s) and/or test individual can be used. In cases where the agent causes a change in pupil diameter in an individual with Alzheimer's Disease but no change in pupil diameter in a control individual (or where the dosage of the agent is adjusted to give the same effect), the agent can be administered to one eye of the test individual, if necessary, the untreated eye serving as the control eye.

It can be readily determined whether an agent which alters neuromuscular signalling in an eye of an individual without Alzheimer's Disease is useful in a diagnostic method (i.e., to identify individuals with Alzheimer's Disease). The agent is administered to a control individual and a test individual in an amount sufficient to alter neuromuscular signalling in the control individual's or test individual's eyes. The agent can be administered to one or both eyes. After a period of time sufficient to alter neuromuscular signalling in the eye of the control individual, the pupil diameter of the eye of the control individual and of the test individual are measured and compared. A change in pupil diameter in the test individual that is greater or lesser than the change in pupil diameter in the control individual indicates that the agent is suitable for use in the method of the present embodiment.

The rate at which a physiological response is affected by an agent which alters neuromuscular signalling will differ in individuals with Alzheimer's Disease compared with normal individuals. Identifying a difference in the rate of response following the administration of an agent which alters neuromuscular signalling of a normal individual compared with the rate in an individual with Alzheimer's Disease can serve as a method of diagnosing Alzheimer's Disease.

Another embodiment of the present invention is a method of diagnosing Alzheimer's Disease in a test individual by determining the rate at which a physiological response is affected by an agent which alters neuromuscular signalling. An agent which alters neuromuscular signalling is administered to the test individual in an amount which causes a physiological response. The rate at which the physiological response is affected is determined. The rate can be determined by measuring how quickly the physiological response changes over time following administration of the agent (e.g., reaches its maximal or minimal value). Alternatively, the rate can be determined by measuring how quickly a physiological response that has been affected by an agent which alters neuromuscular signalling returns to its normal or unaltered state following administration of the agent (e.g., returns to normal from its maximal or minimal value). This rate is compared with the rate at which the physiological response is affected in a suitable control. A rate in the test individual which differs from that in the control (e.g., is more rapid or less rapid) is indicative of Alzheimer's Disease in the test individual.

In a preferred embodiment, the agent is a cholinergic antagonist such as tropicamide. In another aspect, the agent is light. The rate at which the pupil diameter returns to normal diameter in a test individual is determined following the administration of the agent to an eye and the eye's ensuing pupil dilation (when a cholinergic antagonist is administered) or constriction (when light is administered). When the rate at which the pupil diameter returns to normal is slower in the test individual compared with the rate in a suitable control, the result is indicative of Alzheimer's Disease in the test individual.

As discussed above, the pupil diameter measured for the test individual after administration of the agent which alters neuromuscular signalling can be compared with the pupil diameter of a subset of individuals with Alzheimer's Disease, referred to as an "appropriate reference," who have the same attributes as the test individual. In one aspect, the agent is a cholinergic antagonist, for example, tropicamide, that is administered to an eye of the test individual. A pupil diameter for the test individual that is similar to that of the appropriate reference is indicative of Alzheimer's Disease in the test individual. The pupil diameters and attributes of the individuals in the appropriate reference can be stored in a database. In one aspect, the database is stored in a computer and can be searched by computer means, as discussed hereinabove.

Another aspect is a method of determining the reliability of the method of detecting Alzheimer's Disease in an individual. The "reliability" is the ratio of the number of false positives given by the method to the total number of diagnoses. The reliability can also be the ratio of the number of false negatives given by the method to the total number of diagnoses. In this aspect the database additionally includes the increase in pupil diameter in response to the cholinergic antagonist and the attributes of individuals having predementia Alzheimer's Disease, individuals having Alzheimer's Disease without hypersensitivity to cholinergic antagonists (i.e., where the increase in pupil diameter of the test individual is similar to disease free individuals) and individuals having neurodegenerative dementia other than Alzheimer's Disease. The database is searched, preferably, by computer means, for the number of diagnoses of individuals with Alzheimer's Disease without hypersensitivity to cholinergic antagonists and the total number of diagnoses, thereby giving the likelihood of a false negative. Alternatively, the database is searched, preferably by computer means, for the number of test individuals diagnosed by the method of the present invention with predementia Alzheimer's Disease who did not ultimately develop the symptoms of Alzheimer's Disease and the number of test individuals diagnosed with predementia Alzheimer's Disease. The number of false positives given by the test is thereby determined.

Another aspect is a method of determining the likelihood that a test individual diagnosed as having predementia Alzheimer's Disease by the methods of the present invention will develop the symptoms, e.g. dementia, of Alzheimer's Disease within a given period of time. In this aspect, the database additionally comprises the extent of increase in pupil diameter of individuals with predementia Alzheimer's Disease and the extent of the development over time measured periodically of dementia in these individuals. The database is then searched, preferably by computer means, for the likelihood that an individual with predementia Alzheimer's Disease having the increase in pupil diameter of the test individual will develop the symptoms of Alzheimer's Disease in a given period of time, e.g., five years.

Figure 6:
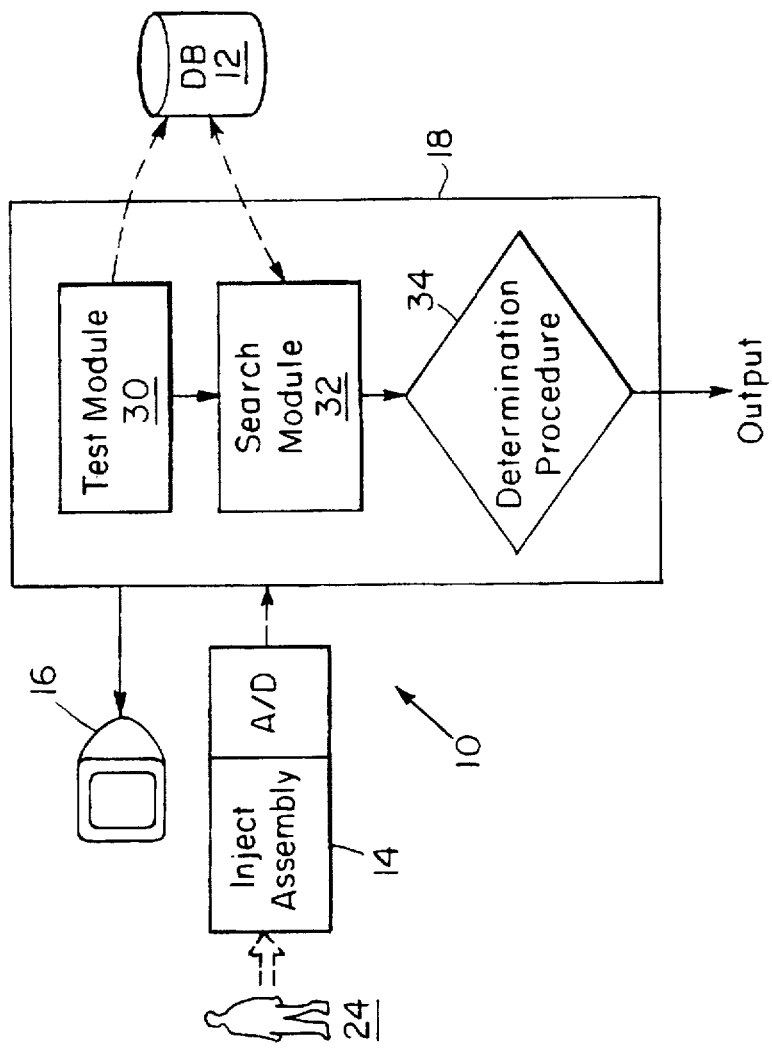
FIG. 6 is a schematic view of a computer hardware implementation in a preferred embodiment of the present invention.

Based on the foregoing study, one implementation of the present invention is as follows and shown in FIG. 6.

In overview, a computer processing system 10 is coupled to a database 12. The computer processing system 10 is of the minicomputer, micro computer, PC type or the like, and operates as a working node in a network (e.g., Local Area Network), as a stand alone workstation or can be connected by modem to a central computer or database. The computer processing system 10 has an input assembly 14 for providing patient information to the memory or computer processor 18 of the computer processing system 10. Similarly, computer processing system 10 includes a monitor 16 and/or other output means. Further, computer processing system 10 has a working memory 18 program (described in detail below) that interacts with database 12 to perform the Alzheimer's testing of the present invention.

Figure 7:
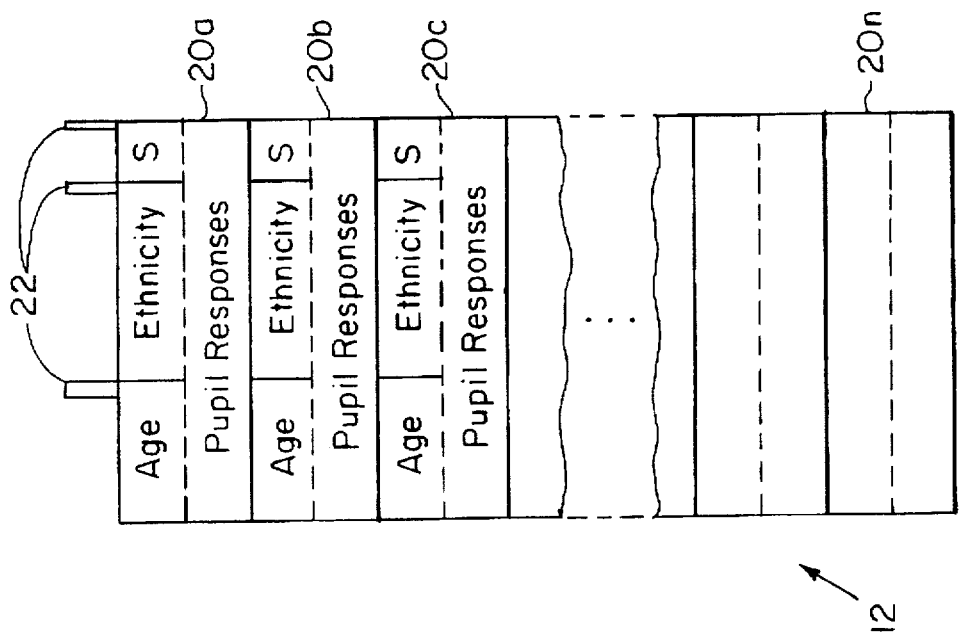
FIG. 7 is a schematic diagram of a database employed in the embodiment of FIG. 6.

To that end, database 12 is either a local storage memory of computer processing system 10 or a remote memory coupled by communication links (telecommunication cables, modems, etc.) common in the art. Referring to FIG. 7, database 12 holds a plurality of records 20 for each person (control subject or test patient). Each record 20 holds information regarding the attributes of the respective person including but not limited to age, sex, ethnic background and physiological responses (including mydriatic responses) as described above in the study which is the basis of the present invention. The database could also include medications, eye color, clinical results, laboratory results, imaging results, family history and the like. The database could also be used to ensure that the readings are in the correct range and, if not, to repeat the study.

Each category of information in a record 20 is indexed for search purposes. That is, the multiple indices 22 enable the database 12 to be searched to find a subset of records 20 having similar information in one or more categories as desired. For example, records of those having the same age range and similar mydriatic responses may be searched and found by the age index 22 in combination with the pupil response index 22.

Accordingly, database 12 may be structured as an indexed sequential file, relational database or similar database having multiple indices for searching across one or more categories of information held in the records 20.

Referring back to FIG. 6, the working memory 18 of computer processing system 10 includes a test module 30, a search module 32 and a determination procedure 34 among other processing means. Test module 30 gathers the patient information including physiological responses (e.g. pupil responses) in accordance with the above described study using an agent which alters neuromuscular signalling, for example an acetylcholine receptor antagonist, such as tropicamide. Upon gathering the data, test module 30 records and stores the same in appropriate records 20 of database 12.

Search module 32 implements user desired searches of database 12 utilizing indices 22 as described above. In particular, in response to input of a user query on database 12, search module 32 formulates a search sequence and activates a search on database 12 using the search sequence. Results of the search are communicated from database 12 to search module 32. In turn, search module 32 provides the search results to a determination procedure 34, which is interactive with the user who input the initial query. Alternatively, determination procedure 34 may be preprogrammed such that no user interaction is solicited by determination procedure 34.

The purpose of determination procedure 34 is basically to compare physiological responses (e.g. mydriatic responses) of Alzheimer's Disease patients and control groups whose records have been extracted from database 12 (by search module 32) to that of the subject being queried. Determination procedure 34 provides results of the comparison as output of processor 18. That is, if the physiological responses of the subject are similar to those recorded in the extracted records of database 12, then a finding or detection of Alzheimer's Disease in the subject is indicated by procedure 34.

The above-described apparatus/system is then used as follows for diagnosing Alzheimer's Disease.

Using input assembly 14, a user 24 (doctor, medical assistant, technician, etc.) initializes the system 10 for a desired patient. Included in the initialization is inputting of patient name, attributes, (e.g. sex, ethnic background, age or age group) and any other information (e.g., antagonist used for testing) desired by the user.

In response to the initialization input, the system 10 and processor program 18, through the test module 30 opens a new record 20 in the database 12. Specifically, test module 30 formats (i.e., indexes) new record 20 with the patient name and attribute information input by the user as illustrated in FIG. 7. The test module 30 also provides and indexes a portion of the new record 20 for test data to be obtained from the patient. Now the system 10/program 18 (and new record 20) is ready to receive test data for the patient.

Once the patient has been prepared for testing as in the above described examples, the system 10 obtains measured responses (i.e., physiological responses) to the antagonist administered to the patient.

In one embodiment the agent which alters neuromuscular signalling is a cholinergic antagonist (e.g. tropicamide) and the physiological response is pupil dilation (i.e. a mydriatic response). The response can be measured periodically after administration of the antagonist, for example at 15, 22, 29 and 41 minutes post-administration of the antagonist. Near infrared light can be used to image the eye without causing constriction due to normal light. Measurement and input of the responses may be by manual, mechanical, electronic or a combination of means and methods. As described in the foregoing examples, measurement of the patient responses is by a video based, pupil center to corneal reflection system. The user 24 may read these measurements and manually input them as test data using the input assembly 14. Alternatively, the reflection system may be coupled to input assembly 14 using an analog-to-digital conversion member, as illustrated in FIG. 6. In that case, as patient responses are measured, they are transmitted to the system 10 without further user input/intervention. Where the site of database 12 is remote from the test site, communication and transmission to database 12 may be through telecommunication lines and modems and the like in the above alternatives.

It is understood that other combinations of means and methods for measuring patient responses and inputting (transmitting) measurements to system 10 are in the purview of one skilled in the art given the foregoing alternatives.

However the measured responses are obtained by system 10/program 18, the test module 30 is responsive to the test data. The test module 30 records the test data in the corresponding patient record (i.e., new record 20) opened during initialization for that patient.

After all test data are gathered and entered into database 12/new record 20, the user 24 enters search commands to search module 32 through input assembly 14. In particular, user 24 formulates and inputs a search query of prior tested individuals (whose information is stored in database 12) having similar attributes (e.g., age, sex, ethnicity) as the current patient. In response, search module 32 searches database 12 for those records 20 having index 22 values that meet the user specified attributes (i.e., age range, sex and ethnicity) of the current patient. Copies of the resulting records 20, a subset of all records 20 in database 12, are obtained by search module 32 from database 12.

Search module 32 passes the copies of resulting (subset of) records 20 to determination procedure 34. Either automatically or upon user command, procedure 34 compares the patient physiological responses (e.g. pupil responses) (in new record 20) to the stored physiological responses in resulting records 20. First procedure 34 determines a range of physiological responses from the resulting records 20. If the patient physiological responses are within the range of resulting records' physiological responses (e.g., are near the average+the standard deviation of the resulting records' pupil responses), then procedure 34 outputs a positive indication of Alzheimer's Disease detected in the current patient. Otherwise, procedure 34 outputs a negative indication. Alternatively, if the patient physiological responses are at the edge of the range of resulting records' physiological responses a retest indication may be output, and the like. The determination procedure 34 may use other comparison ranges besides average, median and the like. Likewise, other comparison methods are suitable.

Alterations in certain peripheral physiological responses are indicative of the abnormal functions that are typically found in the brain of an individual with Alzheimer's Disease. Consequently, the degree or extent of difference in the peripheral physiological response in an individual with Alzheimer's Disease compared with that in a control individual is a measure of the degree or extent of deterioration in the brain of individuals with Alzheimer's Disease. Thus, the degree or extent of alteration of the peripheral physiological responses will be indicative of the extent of disease progression.

Administering an agent which causes a differential physiological response in a test individual compared to that in an appropriate control can, therefore, be used to monitor the response of an individual with Alzheimer's Disease to a treatment. If the treatment being used reverses the progression of Alzheimer's Disease in a test individual, the difference in the physiological response between the test individual and a control individual will decrease. If the treatment being used stops the progression of the disease, the difference in the physiological response between the test individual and a control individual should remain the same. If the treatment being used slows the progression of the disease, the difference between the physiological response of the test individual and the control individual should continue to increase, but at a rate slower than would occur without the treatment.

Alternatively, in the method of monitoring the response of a test individual to a treatment to Alzheimer's Disease, the test individual can serve as his/her own reference. If the treatment stops the progression of the disease, the extent or degree of the physiological response before treatment will be the same as after treatment. If the treatment reverses the progression of the disease, the degree or extent of the physiological response after treatment compared with before treatment will be closer to the degree or extent of the physiological response of an individual without Alzheimer's Disease. If the treatment slows the progression of the disease, the rate or extent of the physiological response after treatment will deviate from the degree or extent in an individual without Alzheimer's Disease to a greater extent than before treatment, but the increase in deviation will be less than what is normally observed in individuals with Alzheimer's Disease.

One embodiment of the present invention is a method of monitoring the response of an individual with Alzheimer's Disease to a method of treating Alzheimer's Disease. An agent which causes a differential physiological response in a test individual compared with the response in an appropriate control by altering neuromuscular signalling is administered to a test individual, either an individual with Alzheimer's Disease, an individual without Alzheimer's Disease, or both. An amount of the agent is used which is sufficient to cause a physiological response in an individual, either an individual with Alzheimer's Disease, an individual without Alzheimer's Disease, or both. After a period of time sufficient for the agent to alter neuromuscular signalling in an individual, the extent of the physiological response is assessed or quantified in the test individual. The extent of physiological response in the control and the test individual are compared and the difference, referred to as the first difference, between the two responses is determined. A treatment for Alzheimer's Disease is administered to the test individual in a manner and for a period of time in which the treatment is effective. The agent which alters neuromuscular signalling is administered to the test individual in the amount and for the period of time sufficient to alter neuromuscular signalling in an individual. This amount and period of time are the same as was used in determining the first difference. The extent of the physiological response is assessed and compared to the extent of the physiological response in the control. The difference, referred to as the second difference, between the extent of physiological response in the control and the test individual after treatment is determined. A value for the second difference that is the same as the first difference indicates that the treatment has arrested the progression of the disease. A value for the second difference that is closer to zero than the first difference indicates that the treatment has reversed the progression of the disease. A value for the second difference that is greater than the first difference, but increases at a rate slower than is typically observed for individuals with Alzheimer's Disease, indicates that the progression of the disease has been slowed. The rate of increase typically observed for individuals with Alzheimer's Disease can be determined by methods known in the art for determining disease progression, for example by monitoring the rate of increase for a group of individuals with Alzheimer's Disease who are not being treated (Davis et al., *The New England Journal of Medicine*, 327:1254 (1992)).

In some instances an agent may cause a physiological response in a test individual but not in a control individual. Alternatively, the agent can be administered in an amount which causes no detectable response in the control individual and causes a quantifiable response in an individual with Alzheimer's Disease. In these cases, the response of an individual to a treatment is monitored by measuring the degree of physiological response. When the degree of response after treatment decreases, remains the same, or increases at a rate less than observed for individuals with Alzheimer's Disease without the treatment, the progression of the disease has been reversed, stopped or slowed, respectively.

In the method of monitoring the response of an individual with Alzheimer's Disease to a treatment for Alzheimer's Disease, the agent which alters neuromuscular signalling is a cholinergic antagonist, an adrenergic agonist or an adrenergic antagonist which can alter neuromuscular signalling in the eye such as tropicamide. Preferably, the agent is a cholinergic antagonist such as tropicamide. Tropicamide can be administered at a concentration of less than about 0.1%, preferably at about 0.01%. The agent is preferably administered to an eye(s) of the test individual, thereby causing a differential change or response in the pupil diameter of the test individual compared with an appropriate control.

There may also be cholinergic antagonists which increase pupil diameter in individuals with Alzheimer's Disease, but do not change pupil diameter in control individuals. Alternatively, the cholinergic antagonist can be administered in an amount which causes an increase in pupil diameter in individuals with Alzheimer's Disease, but does not change pupil diameter in control individuals. Because eye pupil diameter of a control individual in these instances remains essentially unchanged, an untreated eye of the test individual can be used as a control.

Alternatively, the cholinergic antagonist is administered in an amount sufficient to cause minimal but detectable mydriasis in the eyes of an individual without Alzheimer's Disease. The cholinergic antagonist is administered to one or both eyes of the test individual before and after treatment. The pupil diameter is measured at the same period of time after both administrations. This is a suitable period of time for neuromuscular signalling in the eye(s) to be altered. The differences between the pupil diameter of the eye(s) after administration of the cholinergic antagonist and the pupil diameter of an untreated eye are determined. A difference identical to or less than the difference after treatment compared with before treatment indicates that the treatment has arrested or reversed the progression of Alzheimer's Disease in the individual, respectively. A difference in which an increase after treatment compared with before treatment is less than what is typically observed for individuals with Alzheimer's Disease indicates that the progression of the disease has been slowed.

As used herein, an untreated eye is the eye to which the cholinergic antagonist was not administered. The pupil diameter of the untreated eye can be determined before, during or after the administration of the cholinergic antagonist to the treated eye. Alternatively, the untreated eye can be an eye to which the cholinergic antagonist was administered, in which case pupil diameter is measured when neuromuscular signalling in the eye is not being altered by the cholinergic antagonist. The cholinergic antagonist can be administered to one or both eyes of the test individual.

As used herein, "monitoring the response of an individual with Alzheimer's Disease to a treatment for Alzheimer's Disease" means determining whether the method of treatment slows, arrests or reverses the progression of Alzheimer's Disease, as indicated by the progression of symptoms such as dementia. That the degree or extent of a differential physiological response, such as pupil dilation as a consequence of the administration of a cholinergic antagonist, correlates with the progression of Alzheimer's Disease can be readily demonstrated. The extent or degree of the differential physiological response is compared to the progression of Alzheimer's Disease as determined by conventional neuropsychological tests for memory and cognitive deterioration, for example, the Information-Memory-Concentration subtest of the Blessed Dementia Rating Scale or the Mini Mental Status Exam (Corey-Bloom et al., *Neurology*, 45:211 (1995)). A showing that a correlation exists between the extent or degree of the differential physiological response and the progression of the disease as determined by these conventional tests confirms that the extent or degree of the differential physiological response is an accurate measure of Alzheimer's Disease progression. Making this correlation will allow the method of monitoring the response of an individual with Alzheimer's Disease to a method of treatment for Alzheimer's Disease to be used prior to the onset of symptoms, such as dementia. Because conventional tests measure symptoms such as dementia, they cannot monitor the effectiveness of treatments before the appearance of these symptoms. The method of monitoring the response of an individual to a treatment for Alzheimer's Disease also has the advantage that it is less laborious and time consuming than the cognitive tests used in conventional methods of determining the severity of the disease. In addition, the eye test is not subject to variability caused by, for example, the subject's emotional status, depression and variability induced by the tester.

The method of monitoring the response of an individual to a treatment for Alzheimer's Disease can be used for many kinds of treatments. In particular, it can be used to monitor the effectiveness of drug treatments, such as Tacrine (COGNEX®), which is an inhibitor of acetylcholinesterase, the enzyme that degrades the neurotransmitter acetylcholine. The method can be used to monitor other treatment methods such as surgical intervention or the administration of dietary supplements, which are developed in the future to treat Alzheimer's Disease. It should also be possible to monitor patient progress when different kinds of treatments (e.g. drug and surgical) are used in combination as well as when drug combinations are used to treat an individual with Alzheimer's Disease.

Another embodiment of the present invention is a method of a identifying a new treatment which is effective in treating Alzheimer's Disease. Differential physiological responses in the periphery mirror the pathological abnormalities in the brain that are associated with Alzheimer's Disease. Therefore, treatments which slow, arrest or reverse the difference in physiological response in the periphery between test individuals and control individuals should also be agents which slow, arrest or reverse the pathological abnormalities in the brain indicative of Alzheimer's Disease. The method of identifying new agents for the treatment of Alzheimer's Disease comprises the same steps as the method of monitoring the response of an individual with Alzheimer's Disease to a treatment for Alzheimer's Disease except that a test or experimental treatment is used instead of a treatment that is known to be effective in treating Alzheimer's Disease. "Effective in treating Alzheimer's Disease" means slowing, arresting or reversing the progression of symptoms characteristic of the disease.

As with the method of monitoring the response of an individual to a treatment, the method of identifying a new treatment for Alzheimer's Disease can identify a new agent, surgical approach or dietary change, and combinations thereof. It can also include improving known treatments, such as adjusting the dosage, regimen or mode of administration of an agent known to be effective in treating the disease. In this case, an improvement in a known treatment would be indicated if the modification in the treatment results in a smaller differential response than the old treatment.

Recently, the construction of transgenic animal models for testing potential treatments for Alzheimer's Disease has been reported in Wadsworth et al., WO 93/14,200 and Cordell et al., U.S. Pat. No. 5,387,742, the teachings of which are incorporated herein by reference. These transgenic animals can be used to screen compounds for their efficacy in treating Alzheimer's Disease. The ability of test drugs to alter the pathological course of Alzheimer's Disease is measured by the effect of a test compound on the amount and histopathology of amyloid precursor protein and β-amyloid peptide in the transgenic animals and by behavior alterations. These methods are time consuming and expensive. The methods described herein for identifying new treatments for Alzheimer's Disease by administering to an individual an agent which causes a differential response are equally applicable to the transgenic animal models, and are easier and more cost effective than present methods.

Another embodiment is a method of identifying new agents for the treatment of Alzheimer's Disease using animal models. The method comprises the same steps as the method described above in which the test agent is administered to an individual, except that the agent is administered to a transgenic animal model. Cholinergic antagonists are preferred, for example tropicamide.

An agent which causes a differential physiological response in an individual with Alzheimer's Disease can be used to identify a second more sensitive agent which can be used in the methods of the present invention of testing for Alzheimer's Disease in an individual. "More sensitive" means that the difference in the degree of physiological response between a control individual and a test individual caused by the second agent is greater than the first agent, referred to as the "diagnostic agent". A more sensitive agent will permit the diagnosis of Alzheimer's Disease at an earlier stage in the disease process, preferably before the onset of the symptoms. Earlier diagnosis will permit earlier intervention with treatments, thereby delaying the dementia associated with Alzheimer's Disease longer than with a later intervention or even preventing the onset altogether. In addition, agents which are more sensitive are also desirable for use in the method of monitoring the response of an individual being treated for Alzheimer's Disease. The use of more sensitive agents for monitoring a treatment allows a more accurate determination of whether the treatment is slowing, halting or reversing the progression of the disease. It therefore aids in the selection between different treatments, e.g., the selection between different drugs and dosage levels.

In the method of identifying an agent which is more sensitive in diagnosing Alzheimer's Disease than known agents, a diagnostic agent which is known to cause a differential response in an individual with Alzheimer's Disease is administered to an individual with Alzheimer's Disease in an amount sufficient to cause the differential response. The degree of physiological response is then assessed after a period of time sufficient to allow the agent to cause the differential response. Preferably, the amount of diagnostic agent and the period of time are chosen so that the maximal differential physiological response is being assessed. The difference, referred to as the first difference, between the degree of physiological response caused by the diagnostic agent in the individual with Alzheimer's Disease and in a control individual is determined. After the effects of the agent have worn off, a test agent being tested for being more sensitive in diagnosing Alzheimer's Disease is administered to the same individual with Alzheimer's Disease in an amount at which the test agent is expected to cause the same differential response. The degree of the physiological response is assessed after a period of time in which the agent being tested is expected to cause the differential physiological response. The difference, referred to as the second difference, between the degree of physiological response caused by the test agent in the individual with Alzheimer's Disease and the degree of physiological response caused by the test agent in a control individual is determined. A value closer to zero for the first difference compared with the second difference indicates that the test agent is more effective than the diagnostic agent in diagnosing Alzheimer's Disease. Alternatively, the test agent can be administered to the individual with Alzheimer's Disease before the diagnostic agent.

Preferably, the diagnostic agent is a cholinergic antagonist which causes a greater degree of pupil dilation in a test individual compared with a control individual following administration of the agent to an eye of the test individual and to an eye of the control individual. A preferred cholinergic antagonist is tropicamide. An agent being tested for being more sensitive is administered to an eye, referred to as the test eye, of an individual with Alzheimer's Disease. An agent, referred to as the diagnostic agent, which is known to cause a greater increase in pupil diameter in an eye of a test individual compared to a control individual is administered to an untreated eye, referred to as the control eye, of the individual with Alzheimer's Disease. A sufficient amount of the diagnostic agent is administered to cause an increase in pupil diameter in the eye of the control individual. Preferably, the amount of diagnostic agent used is the amount which causes the maximum differential response between a test individual and a diagnostic individual. When tropicamide is the diagnostic agent, typically, a concentration of less than about 0.1% is used, preferably about 0.01%. After a period of time sufficient to alter neuromuscular control in the control eye, the pupil diameter of the control eye and the test eye are measured and compared. Preferably, the period of time is chosen so that the maximum change in pupil diameter is being measured, either in the control eye or test eye. A greater increase in the pupil diameter of the test eye compared with the control eye indicates that the agent being tested is more sensitive than the diagnostic agent.

The diagnostic agent and the agent being tested can be administered to the respective eyes simultaneously. Alternatively, the diagnostic agent and the agent being tested can be administered at different times to the same eye(s) or different eyes. If the agent being tested and the diagnostic agent are administered to the same eye(s) at different times, it is necessary that a sufficient period of time elapse between the administration of the two agents to allow neuromuscular signalling in the eye to return to normal. The test agent and/or diagnostic agent can also be administered to both eyes of the individual with Alzheimer's Disease, as long as the two agents are administered at different times, as described above.

The present invention also relates to a kit comprising an agent which causes a differential physiological response in the periphery of an individual with Alzheimer's Disease compared with the response in an individual without Alzheimer's Disease and an apparatus for administering the agent to an individual. In one embodiment, the agent is a cholinergic antagonist, an adrenergic agonist and an adrenergic antagonist. The apparatus is a dispenser for administering the agent to the eye of an individual. In a particular embodiment, the agent is a cholinergic antagonist such as tropicamide.

The invention is further illustrated by the following examples, which are not intended to be limiting in any way.

EXEMPLIFICATION

EXAMPLE 1

The mydriatic response to administration of the cholinergic antagonist tropicamide was studied in 5 patients diagnosed as probable Alzheimer's patients. In addition, 13 negative control patients who did not exhibit symptoms characteristic of Alzheimer's Disease were included in the study.

Subjects had normal findings on a brief neurological examination and a bedside neuro-ophthalmological examination that evaluated saccades, smooth pursuit, visual fields to confrontation and partial field optokinetic nystagmus. All subjects' pupils were examined for a narrow angle anterior chamber to eliminate subjects at risk for narrow angle glaucoma. Subjects were disqualified from participation if they had small pupils (less than 2 mm diameter), unusual pupil shapes, star cataracts or incipient cataracts that might affect accurate measurement of pupil diameter. All non-demented controls had normal findings on a short neuropsychological battery and no diseases of the central nervous system by history. Medication use in patients and controls was comparable. No subject was taking medications with known interaction effects with tropicamide.

Pupil diameter was measured using an Applied Science Laboratories video based, near infrared pupil center to corneal reflection system. This system, used to measure eye movements, also measures pupil diameter sampled continuously at 60 hertz. The system is non-invasive and requires no subject attachments or restraints. For this study, subjects were seated in a comfortable room with dim ambient illumination 1.5 m in front of a TV screen.

The subjects' pupils were imaged by the system as they sat viewing the TV screen set at a uniform low illumination. Subjects were directed to look at the center of the screen while the eye was initially imaged. Once the eye was adequately imaged and subjects had ample time to adjust to ambient illumination, a short calibration procedure was run to ensure accurate monitoring of subjects' eye position.

A very dilute solution of tropicamide (0.01%) was used to induce pupil dilation in this trial. Tropicamide in a solution strength of 0.5 to 1.0% induces maximal mydriasis in 20 to 40 minutes in normal healthy subjects. The short action time of this agent was chosen to limit the time required to reach a maximal mydriatic response. After baseline pupil measurements were determined for each eye, a single drop of the tropicamide solution was added to one of the eyes (randomly chosen). Pupil diameter data was sampled from both eyes for 30 second epochs over the course of an hour at 0, 2.5, 8, 15, 22, 29, 41 and 53 minute intervals. Between measurement epochs, subjects were shown segments from the video tape Fantasia in order to reduce anxiety, fatigue and boredom from sitting in a semidarkened room.

The percent change in diameter in the treated versus the untreated eyes was compared for all patients. Dependent variables consisted of the overall percent change from baseline in the treated and untreated eyes, and the percent change in treated and untreated eyes compared to baseline at each sampling interval. The Mann-Whitney one tailed test was used for all between group comparisons. The observed data are reported in FIG. 1 which shows the pupil diameter measurements observed in the treated eyes of both probable Alzheimer's patients and non-demented controls. The pupil diameter determinations for untreated eyes of non-demented and probable Alzheimer's patients were substantially identical.

These data demonstrate that the overall dilation effect seen in probable Alzheimer's patients was significantly greater than that observed in the non-demented controls. Data for probable Alzheimer's Disease patients are significant at p<0.05 level beginning at 15 minutes. No differences were found for the untreated eye at any sampling epoch or for the mean change over the seven sampling epochs.

EXAMPLE 2

Fifty eight individuals were tested for their pupil response to a very dilute solution of tropicamide. These subjects were divided into 5 experimental groups: two patient groups and three groups of elderly controls. The Alzheimer's patient group consisted of 14 subjects who had been previously diagnosed with probable Alzheimer's Disease based on standard clinical criteria. A pilot sample of non-Alzheimer's type dementias consisted of 4 patients with a diagnosis of Korsakoff's syndrome, multi-infarct dementia and dementia with an extrapyramidal syndrome. Based on neuropsychological screening criteria defined prior to the initiation of the study, 40 elderly subjects were assigned to one of 3 groups. Normal elderly controls consisted of 32 subjects who performed at or above age norms on a battery of neuropsychological tests, that assessed intellectual capacity, attention, memory and language. Five subjects whose performance yielded abnormalities in memory and discrepancies between estimated life-long IQ and current performance in cognitive tests were classified as "suspect" Alzheimer's individuals. Three elderly subjects who exhibited abnormal findings on cognitive tests but had no salient memory deficit were classified as "cognitively abnormal", elderly for this study.

Prior to testing, subjects were seated in a comfortable semi-darkened room 1.5 meters in front of a TV screen and given sufficient time for the eyes to accommodate to the dim illumination. After resting pupil diameter (baseline) measurements were recorded for 1 minute from each eye, a single drop of a very dilute solution of tropicamide (0.01%) was administered to one eye (arbitrarily chosen) and a drop of a control solution (sterile water) to the other eye. The concentration of tropicamide was chosen so as to cause minimal dilation of normal eyes. The experimenter placing the drops was blind to which solution was being applied to which eye. Pupil diameter data were obtained from each eye for 30 sec samples at 2, 8, 15, 22, 29 and 51 minutes. Pupil diameter was measured with a video based, pupil center to corneal reflection, system capable of measuring eye position and pupil diameter (Applied Science Laboratories, Waltham, Mass.). Sampling rate was 60 hertz, yielding 1800 samples per 30 second measurement cycle. Between measurement intervals, subjects were shown segments from the video tape Fantasia in order to reduce anxiety, fatigue, and boredom from sitting in a semi-darkened room.

Figure 2:
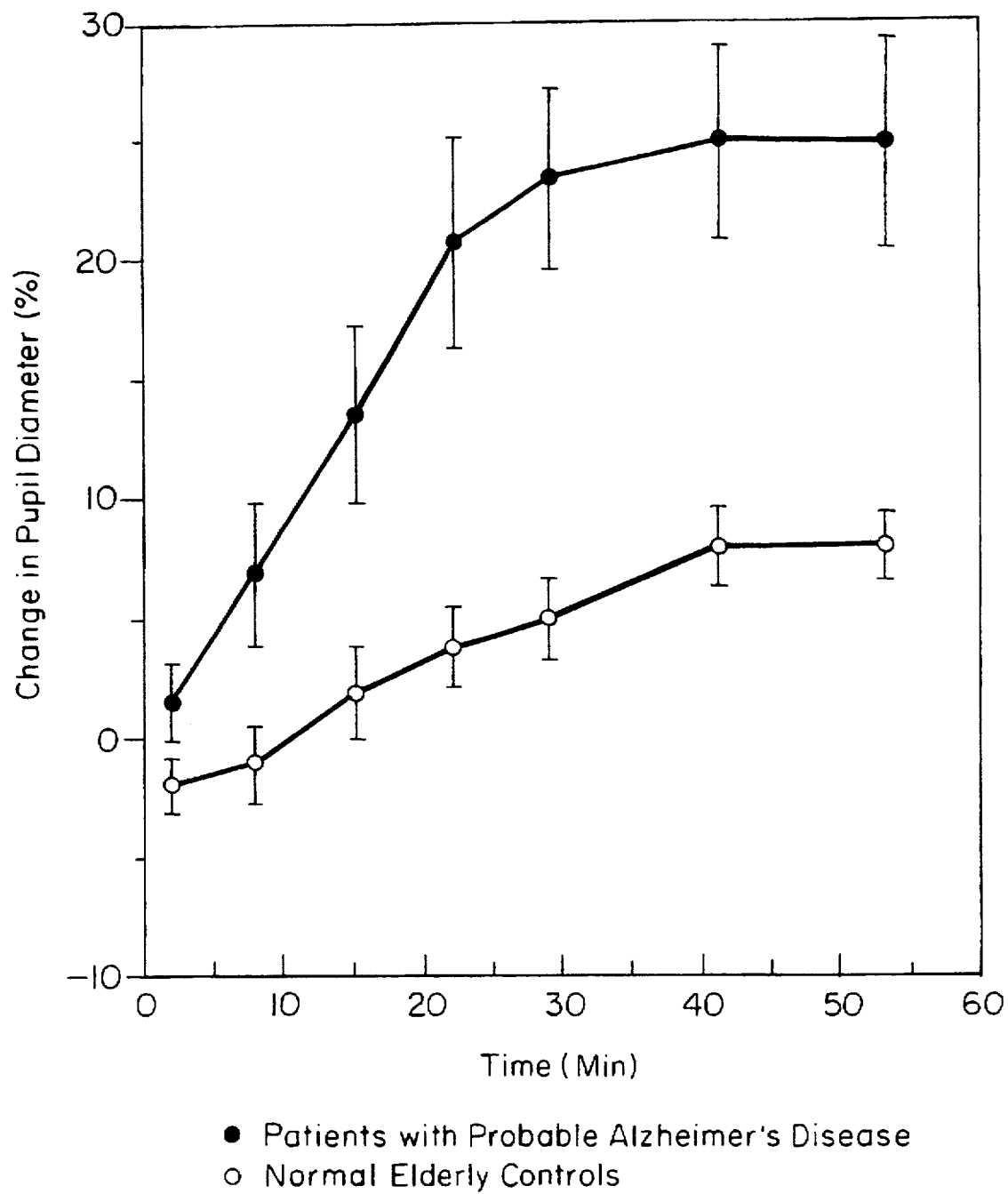
FIG. 2 is a graph of the percentage change in pupil dilation response to the acetylcholine receptor antagonist tropicamide in Alzheimer's Disease patients and experimental control groups. Each time point represents the mean percentage change in pupil diameter over resting pupil diameter (baseline) measurement in the treated eye of Alzheimer patients (●) and normal elderly controls (○)

FIG. 2 compares the pupil dilation response over the baseline diameter of patients with clinically diagnosed Alzheimer's Disease and experimental controls to the acetylcholine receptor antagonist tropicamide. As expected, the treated pupils of the normal elderly controls (lower curve) showed a minimal increase in pupil diameter over the course of the hour. In contrast, the patients clinically diagnosed with Alzheimer's Disease displayed a pronounced response to the pupil dilating effect of tropicamide as shown by the upper curve in FIG. 2. A Kurskal Wallis pairwise multi-sample test was used to determine the significance of the differential tropicamide sensitivity of the Alzheimer's and control groups. Overall the results indicated that at minute 29 there is a 23.4% (SEM 3.8%) change in the pupil diameter of patients with probable Alzheimer's Disease compared to a 5% (SEM 1.7%) change for normal elderly subjects (p=0.009).

Figure 3:
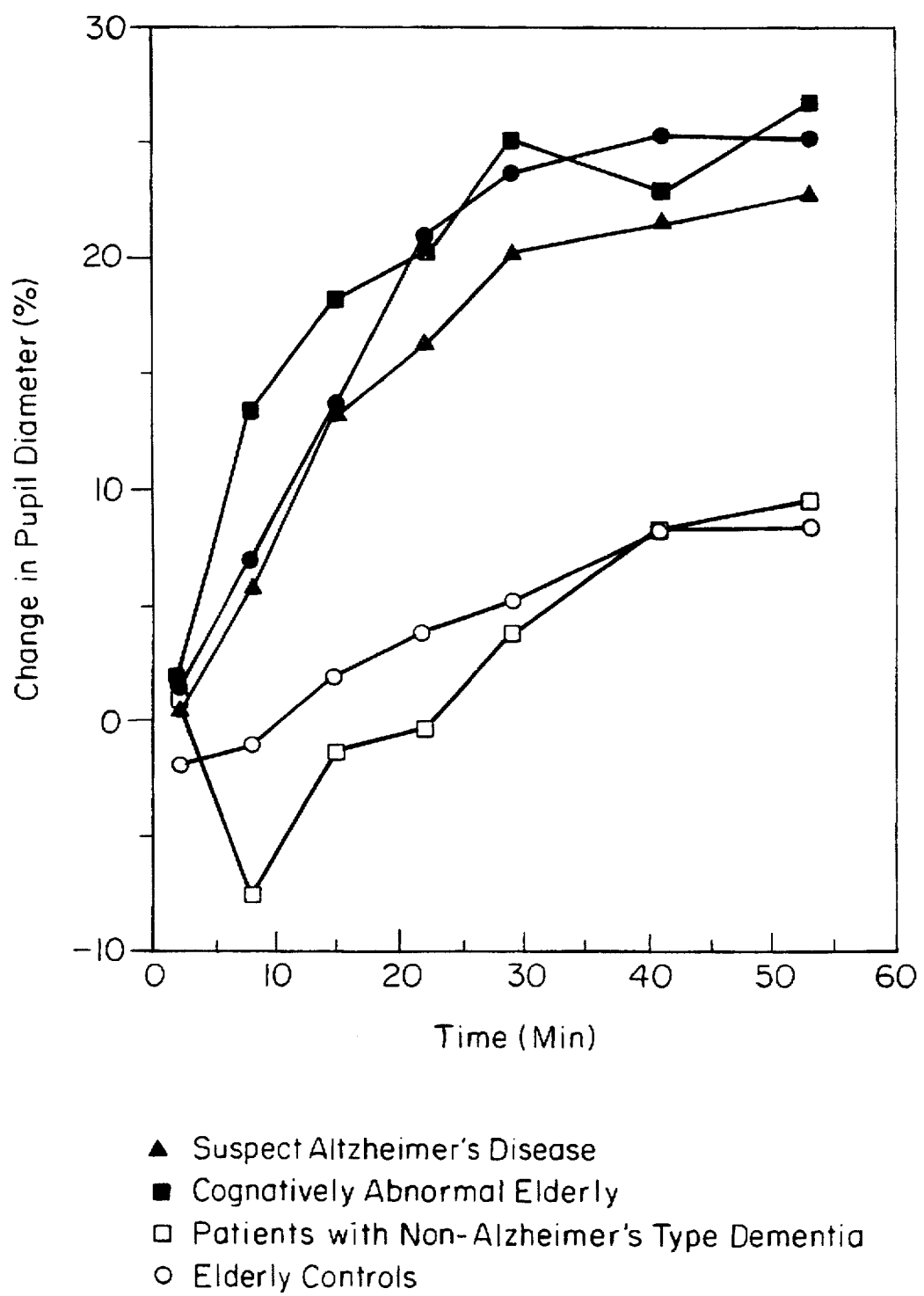
FIG. 3 is a graph of the percentage change over time in pupil diameter of the treated eye over baseline of the suspect Alzheimer's subjects (▲), the cognitively abnormal elderly (■), patients with probable Alzheimer's Disease (●), patients with non-Alzheimer's type dementia (□) and normal elderly controls (○).

FIG. 3 compares the response of patients with clinically diagnosed Alzheimer's Disease, the suspect Alzheimer's individuals, the cognitively abnormal elderly subjects, the patients with non-Alzheimer's type dementia, and the normal controls. Both the suspect Alzheimer Disease individuals and the cognitively abnormal elderly subjects show an almost identical pattern of pupillary response to that of patients with clinically diagnosed Alzheimer's Disease. In contrast the response of the group of patients diagnosed with non-Alzheimer's type dementia is similar to the performance of the normal elderly controls.

Figure 4:
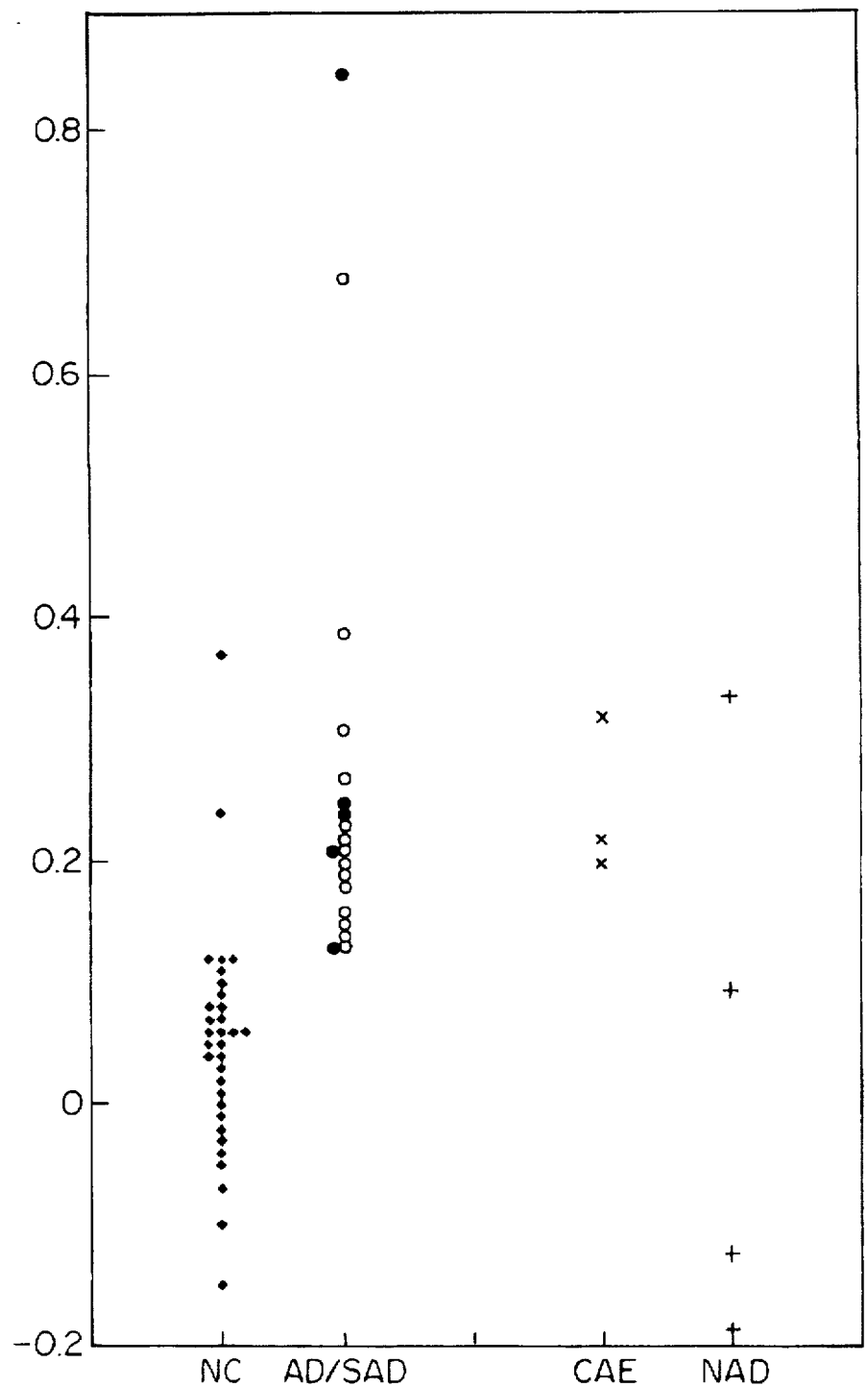
FIG. 4 is a graph of individual pupil dilation scores at minute 29 for patients with probable Alzheimer's Disease and all control subjects. Each symbol represents the percent change in pupil size over baseline of a single individual. "NC" indicates normal control, "AD" indicates individuals with Alzheimer's Disease, "SAD" indicates suspect Alzheimer's Disease individuals, and "CAE" indicates cognitively abnormal elderly individuals.

The complete set of data for the 29 minute sampling point (the point of maximal separation of clinically diagnosed Alzheimer's patients and normal elderly control subjects) is presented in FIG. 4. Each symbol represents the percent change in pupil size over baseline of a single individual. A minimum overlap in the pupil dilation scores between groups and between individual subjects in different groups is obtained by designating 13% change in pupil diameter at minute 29 of the assay as a cutoff point.

Figure 5:
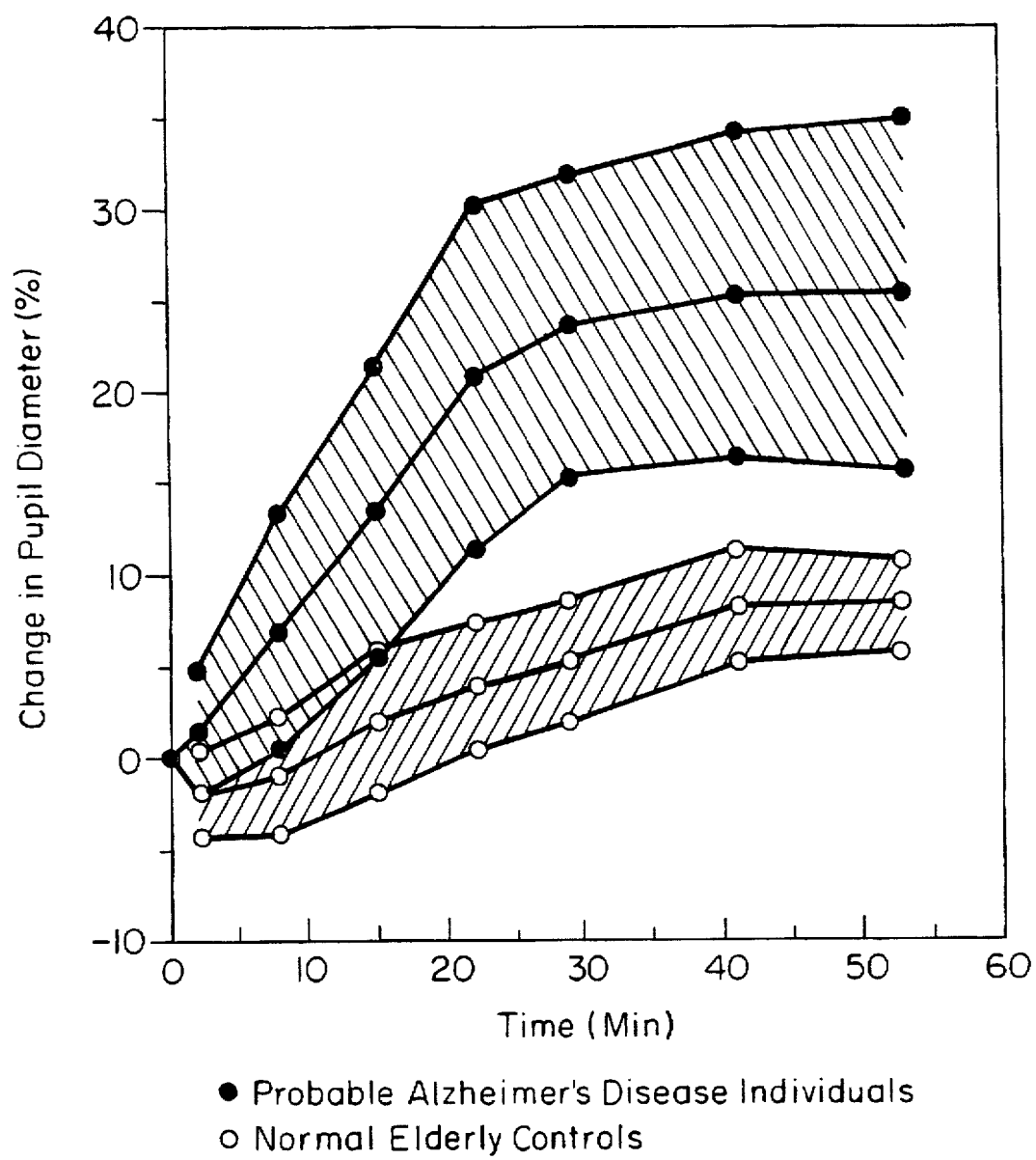
FIG. 5 is a graph of the mean percentage change in pupil dilation with ±95% confidence intervals for patients with probable Alzheimer's Disease and normal elderly controls. Closed boxes indicate individuals with probable Alzheimer's Disease. Open boxes indicate normal elderly controls.

FIG. 5 plots the means and the ±95% confidence intervals of the means for patients with probable Alzheimer's Disease and the normal elderly controls. There is a clear separation between these groups beginning at minute 15. This distinct separation between the groups is maintained at minute 29 after instillation for the ±99% intervals (not shown).

These graphs indicate that with few exceptions, discussed below, both patients with a diagnosis of probable Alzheimer's Disease and the subjects classified as "suspect" Alzheimer's individuals can be distinguished from the normal elderly controls on the basis of their hypersensitivity to tropicamide. Furthermore, the fact that the response of patients with non-Alzheimer's type dementias is similar to that of normal elderly controls, suggests that the pupil dilation assay may be specific for Alzheimer's pathology.

When the data from the 14 patients with probable Alzheimer's Disease is combined with the 5 subjects classified as suspect Alzheimer's individuals, 18 of 19 exhibited a positive response to the pupil dilation assay.

Several findings from this study show that the tropicamide pupil dilation test is able to identify Alzheimer's patients prior to the onset of clinical symptoms of dementia. First, patients with a clinical diagnosis of Alzheimer's Disease who exhibited an exaggerated mydriatic response included the most mildly demented individuals as measured by the Information-Concentration-Memory subtest of the Blessed Dementia Rating Scale. No correlation was found between patients' dementia scores and a positive pupil result. The lack of such a correlation is consistent with the pupil assay being sensitive to the earliest stages of the disease. Secondly, almost all elderly subjects living in the community who were tested and who showed a positive pupil response also exhibited neuropsychological deficits and most were found to have a salient memory impairment consistent with Alzheimer's Disease.

Of particular interest is the case of patient SG. This elderly subject living in the community initially exhibited a positive pupil response to tropicamide but showed no obvious cognitive deficits and only a self report of mild difficulty with some daily living activities. He was re-tested nine months later and continued to show a positive pupil response. During this interval he exhibited a substantial decline (from 0 to 6) on the Information-Concentration-Memory subtest on the Blessed Dementia Rating Scale and developed clear memory deficits. These results indicate that the pupil dilation assay was sensitive enough to detect an abnormal response in an elderly community-dwelling individual who subsequently developed symptoms consistent with a diagnosis of probable Alzheimer's Disease.

Of the 40 elderly subjects from the community that were tested, normal elderly controls, suspect Alzheimer's dementia individuals, and cognitively abnormal elderly subjects 9 showed a positive response to the assay that was ≧13% at minute 29, of which 7 were either in the suspect Alzheimer's Disease group or the cognitively abnormal elderly group. Thus, only 2 of 32 normal elderly controls exhibited an exaggerated positive pupil response to the assay, but had no other clinically notable cognitive or neurological defects. This number of positive pupil responses in the "normal" elderly sample is within the order of magnitude one should expect from previous studies of the prevalence of this disease in the community. It is therefore possible that these 2 individuals may, like subject SG, have sufficient Alzheimer's pathology to register a positive pupil finding but do not yet exhibit clinically discernible symptoms of cognitive decline.

Of the 4 patients with non-Alzheimer's type dementia (NAD), included as a pilot sample, 3 showed a minimal response to the pupil assay and reacted in the same way as the normal elderly sample. One subject (diagnosed with Korsokoff's syndrome) exhibited a pupil response similar to that of patients with probable Alzheimer's Disease.

EQUIVALENTS

Those skilled in the art will know, or be able to ascertain using no more than routine experimentation, many equivalents to the specific embodiments of the invention described herein. These and all other equivalents are intended to be encompassed by the following claims.

What is claimed is:

1. A method of testing for Alzheimer's Disease in an individual, comprising the steps of:
    a) administering to an individual being tested for Alzheimer's Disease, referred to as a test individual, a drug selected from the group consisting of: adrenergic agonists and adrenergic antagonists, wherein the drug is administered in an amount sufficient to cause a physiological response in an individual;
    b) assessing in the test individual the physiological response to the drug; and
    c) comparing the extent of the physiological response determined in step b) in the test individual with the extent of the physiological response in an appropriate control, wherein a greater response or lesser response in the test individual compared with the response in the control is indicative of Alzheimer's Disease in the test individual.

2. The method of claim 1 wherein the physiological response assessed is selected from the group consisting of: sweat production, saliva production, heart rate, blood pressure and change in pupil diameter in the eyes.

3. A method of testing for Alzheimer's Disease in an individual, comprising the steps of:
    a) administering to an individual being tested for Alzheimer's Disease, referred to as a test individual, an agent which alters neuromuscular signalling in an eye of an individual in an amount sufficient to cause a change in pupil diameter in the eye of an individual with the proviso that the agent is not a cholinergic antagonist or cholinergic agonist;
    b) measuring the pupil diameter of the eye of the test individual after a period of time sufficient for the agent to alter neuromuscular signalling in the eye an individual; and
    c) comparing the pupil diameter of the eye of the test individual determined in step b) with the pupil diameter determined from an appropriate control, wherein a greater or lesser change in the pupil diameter in step b) compared with the control is indicative of Alzheimer's Disease in the individual being tested for Alzheimer's Disease.

4. The method of claim 3 wherein the agent is selected from the group consisting of: adrenergic agonists or antagonists, acetylcholinesterase inhibitors, agonists and antagonists of intracellular signalling systems, agonists and antagonists of neuromodulatory systems, agonists and antagonists of calcium metabolism and calcium channels, and agonist and antagonists of sodium and potassium channels involved in nerve and muscle function.

5. The method of claim 3 wherein the agent is selected from the group consisting of: adrenergic agonist and adrenergic antagonist.

6. A method of testing for Alzheimer's Disease in an individual, comprising the steps of:
    a) administering to an eye of an individual being tested for Alzheimer's Disease, referred to as a test individual, a cholinergic antagonist in an amount sufficient to cause dilation of the pupil in the eye;
    b) after a period of time suitable for the pupil of the eye to dilate, measuring the rate at which the pupil returns to its normal diameter;
    c) comparing the rate determined in step b) with the rate at which the pupil returns to its normal diameter from an appropriate control, wherein a rate determined in step b) which is slower than the rate determined from the appropriate control is indicative of Alzheimer's Disease in the test individual.

7. The method of claim 6, wherein the agent is tropicamide.

8. A method of testing for Alzheimer's Disease in an individual, comprising the steps of:
    a) administering to an individual being tested for Alzheimer's Disease, referred to as a test individual, an agent selected from the group consisting of: cholinergic agonist, cholinergic antagonists, adrenergic agonists and adrenergic antagonists, the agent being administered in an amount sufficient to cause a physiological response in an individual;
    b) assessing in the test individual the physiological response to the agent; and
    c) comparing the extent of the physiological response determined in step b) in the test individual with the extent of the physiological response to the agent in individuals with Alzheimer's Disease and wherein the individuals have attributes similar to the test individual, wherein the extent of the physiological response of the test individual compared to the extent of the physiological responses of the individuals with Alzheimer's Disease indicates whether the test individual has Alzheimer's Disease.

9. A method of testing for Alzheimer's Disease in an individual, comprising the steps of:
    a) administering to an individual being tested for Alzheimer's Disease, referred to as a test individual, a cholinergic antagonists administered in an amount sufficient to cause a physiological response in an individual;

b) assessing in the test individual the physiological response to the agent; and c) comparing the extent of the physiological response determined in step b) in the test individual with the extent of the physiological response to the agent in individuals with Alzheimer's Disease recorded in a database, wherein the individuals have attributes similar to the test individual, wherein the extent of the physiological response of the test individual compared to the extent of the physiological responses of the individuals with Alzheimer's Disease indicates whether the test individual has Alzheimer's Disease.

10. The method of claim 9 wherein the agent is administered to an eye and the physiological response is an increase in pupil diameter.

11. The method of claim 9 wherein the cholinergic antagonist is tropicamide.

12. The method of claim 9 wherein the attributes of the individuals from various population groups comprise age, ethnicity and sex.

13. The method of claim 9 wherein the extent of increase in pupil diameter of the test individual and of the individuals with Alzheimer's Disease are compared by computer means.

14. The method of claim 13 wherein the comparison by computer means comprises the steps of:

a) searching the database for a subset of individuals having attributes similar to the test individual; and b) measuring the extent of increase in pupil diameter of the test individual against the extent of increase in pupil diameter of the subset of individuals.

15. The method of claim 14 wherein the database further includes the increase in pupil diameter in response to the cholinergic antagonist and the attributes of individuals having predementia Alzheimer's Disease, individual's having Alzheimer's Disease with no hypersensitivity to the cholinergic antagonist, and individuals having neurodegenerative disorders or dementia other than Alzheimer's Disease.

16. The method of claim 15 further comprising the step of determining:

i) the occurrence of a false positive where the test individual is a predementia Alzheimer's patient; and ii) the occurrence of a false negative where the extent of increase in pupil diameter in the test individual is the same as in individuals without Alzheimer's Disease.

17. The method of claim 16 wherein the database further comprises:

a) the extent increase in pupil diameter in response to the cholinergic antagonist of the individuals having predementia Alzheimer's Disease; and b) the extent of the development of dementia of the individuals from population groups having predementia Alzheimer's Disease measured periodically after the diagnosis of predementia Alzheimer's Disease.

18. The method of claim 17 further comprising determining the likelihood that the test individual will develop dementia within a given time period where the test individual has the same increase in pupil dilation in response to the cholinergic antagonist and the same attributes as the individuals having predementia Alzheimer's Disease.

19. A method of testing for Alzheimer's Disease in an individual, comprising the steps of:

a) administering to an individual being tested for Alzheimer's Disease, referred to as a test individual, a cholinergic agonists administered in an amount sufficient to cause a physiological response in an individual;

b) assessing in the test individual the physiological response to the agent; and c) comparing the extent of the physiological response determined in step b) in the test individual with the extent of the physiological response to the agent in individuals with Alzheimer's Disease recorded in a database, wherein the individuals have attributes similar to the test individual, wherein the extent of the physiological response of the test individual compared to the extent of the physiological responses of the individuals with Alzheimer's Disease indicates whether the test individual has Alzheimer's Disease.

20. In a computer processing system having a digital processor and a working memory, an apparatus for detecting Alzheimer's Disease in an individual, comprising:

a) an input assembly coupled to the digital processor for:

i) monitoring a physiological response of an individual to an agent which alters neuromuscular signalling;

ii) assessing the extent of the physiological response in the individual; and iii) communicating the physiological response to the database;

b) a database linked to the digital processor holding records of the physiological response to the agent by various population groups afflicted with Alzheimer's Disease, wherein each population group has a particular set of attributes;

c) computer means, executed in the working memory by the digital processor, for comparing the determined amount of the physiological response of the individual to responses held in the database, such that the computer means generates on output an indication of whether the individual has Alzheimer's Disease; and d) output means coupled to receive from the computer means the generated indication and for displaying the indication of whether the individual has Alzheimer's Disease.

21. The apparatus of claim 20 wherein the apparatus monitors the physiological response of an individual to a cholinergic antagonist.

22. The apparatus of claim 21 wherein the apparatus monitors the mydriatic response of an individual to a cholinergic antagonist.

23. The apparatus of claim 22 wherein the cholinergic antagonist is tropicamide.

24. The apparatus of claim 23 wherein the input assembly includes means for obtaining percent change in pupil diameter of the eye of the individual.

* * * * *